United States Patent [19]
Atkinson et al.

[11] 3,966,781
[45] June 29, 1976

[54] DEUTERATION OF FUNCTIONAL GROUP-CONTAINING HYDROCARBONS

[75] Inventors: Joseph G. Atkinson, Montreal; Michael O. Luke, Pinawa, both of Canada

[73] Assignee: Merck Sharp & Dohme (I.A.) Corporation, New York, N.Y.

[22] Filed: Dec. 10, 1973

[21] Appl. No.: 423,361

Related U.S. Application Data

[62] Division of Ser. No. 192,296, Oct. 26, 1971, abandoned.

[30] Foreign Application Priority Data

Dec. 17, 1970 Canada............................... 100961

[52] U.S. Cl............................ 260/410.9 R; 260/404; 260/413; 260/491; 260/540; 260/561 R
[51] Int. Cl.².......................................... C11C 3/02
[58] Field of Search............. 260/410.9 R, 413, 491, 260/540, 404, 561 R, 468 R, 468 L

[56] References Cited
OTHER PUBLICATIONS

Heyningen et al. J. Biol. Chem. 125 (1938) pp. 495–500.

Dinh–Nguyen et al. Acta. Chem. Scand. 20 (1966) pp. 1423–1424.

Dinh–Nguyen et al. Acta. Chem. Scand. 13 (1959) pp. 1032–1033.

Bell et al. Chem. Soc. Jour. (1953) pp. 3456–3463.

Primary Examiner—Winston A. Douglas
Assistant Examiner—John F. Niebling
Attorney, Agent, or Firm—Thomas E. Arther; Harry E. Westlake, Jr.

[57] ABSTRACT

Deuterated functional group-containing hydrocarbons prepared by treating the non-labelled substrate in the liquid state with deuterium gas in the presence of a Group VII or VIII metal catalyst with heating between ambient to 300° C. The labelled compounds are especially useful in reaction mechanism studies, as tracers in separation process studies, in the investigation of the physical properties of labelled compounds and in other specialized research work.

10 Claims, No Drawings

DEUTERATION OF FUNCTIONAL GROUP-CONTAINING HYDROCARBONS

This is a division of application Ser. No. 192,296, filed Oct. 26, 1971 now abandoned.

This invention is concerned with deuterated functional group-containing hydrocarbons and a novel method for replacing substantially all hydrogen originally present in the substrate by deuterium. The process for preparing these compounds comprises bringing together a saturated or unsaturated, functional group-containing hydrocarbon having a boiling point of at least 100° C., in the liquid state, and deuterium gas in the presence of a catalyst until such time as the desired percentage of the hydrogen atoms has been replaced by deuterium atoms. The catalyst preferably is supported on a common carrier, and the reaction is carried out at a temperature of from ambient to about 300° C., preferably from 200°–250° C., until the desired degree of deuteration has been effected.

It is accordingly an object of the present invention to provide certain novel deuterated saturated functional group-containing hydrocarbons having a boiling point of at least 100° C. with isotopic purity of between 50 to 99.5 atom % D.

It is also a further object of the present invention to provide a process for preparing such deuterated saturated functional group-containing hydrocarbons.

In accordance with the present invention one can employ an exchange system wherein continuous, automatic cycling of liquid substrate through the catalyst bed co-current with deuterium gas is effected or wherein the labelling gas is passed through a mixture, preferably heated, of the catalyst and the compound to be exchanged, in its liquid form, until the desired degree of deuteration is attained.

The functional group-containing hydrocarbons that can advantageously be perdeuterated by this process are $C_{4-18}$ acyclic saturated or unsaturated ethers, alcohols, mono-, di- or polycarboxylic acids and their esters, as well as amides. Representative examples are $C_{4-18}$ mono-, di- or polyalkanoic, alkenoic or alkynoic acids and their lower alkyl esters and amides, $C_{4-18}$ dialkyl ethers, $C_{4-18}$ alkoxyalkyl ethers [such as glyme, diglyme, triglyme, bis(alkoxyalkyl)ethers and the like], $C_{4-18}$ alkanols, alkenols or alkynols, mono-, di- or polyalkanoic acid esters of alkanols, as well as other usual functional group-containing hydrocarbons of the above varieties. The unsaturated starting substances are deuterogenated by the method of this invention thus forming the saturated, deuterated analog. The process comprises bringing together the desired saturated or unsaturated functional group-containing hydrocarbon in the liquid state and deuterium gas in the presence of a catalyst at temperatures below the boiling point of the hydrocarbon, whereby a hydrogen-deuterium exchange between deuterium gas and the liquid functional group-containing hydrocarbon takes place. Optionally a partially or fully deuterated non-functional group-containing hydrocarbon can be used in this process as a supplementary source of deuterium.

The hydrogen-deuterium exchange between deuterium gas and the functional group-containing hydrocarbon liquid is carried out below the boiling point of said compound and within a temperature range of from ambient to about 300° C. with a preferred temperature range of from 200° to 250° C.

As catalyst there may be used any of the common hydrogenation-dehydrogenation catalysts selected from Group VII and VIII metals, but preferably Group VIII metals. Palladium, platinum, rhodium, ruthenium, osmium, iridium, nickel, rhenium and the like are most advantageously employed although palladium and nickel are uniquely effective. Various supports including carbon, Kieselguhr, alumina, clay and zeolites can be used although carbon and Kieselguhr are preferred. Powdered, pelletized and extruded catalysts can be used, although pelletized and extruded forms are preferred. The amount of catalyst is not critical although generally 2 percent or more of the catalyst on a support, such as activated carbon, has been found to effectively catalyze the conversion of the substrate to the deuterated product.

Dispersion of the deuterium gas in the hydrocarbon liquid is carried out by passing deuterium through a porous glass disk into the stationary catalyst layer of about 5–40 mesh, advantageously 10–30 mesh though the mesh size is not a critical factor and may be of larger or smaller size. The flow of deuterium gas through the liquid functional group-containing hydrocarbon is carried out continuously for a period of time varying with the flow rate of the gas (higher $D_2$ flow rates decrease and lower flow rates increase the time), the number of carbon atoms in the starting substance, its degree of unsaturation, the amount of substrate to be deuterated and the percentage of deuterium it is wished to introduce into the product.

Once the reaction is terminated the deuterated product can be isolated by one or another method depending upon whether the deuterated product is liquid or solid at room temperature. When the deuterated product is liquid at room temperature, it can be allowed to drain from the catalyst or it can be extracted with a low boiling hydrocarbon, for example, pentane or hexane and the solvent then removed by distillation. In either case the deuterated product is purified by distillation under vacuum. When the deuterated product is solid at room temperature it also can be extracted with a low boiling hydrocarbon as mentioned above, the solvent removed by distillation and the solid residue when recrystallized from a low boiling solvent such as pentane and the like.

Various types of exchange reactors can be used in carrying out the method of this invention. One suitable reactor, known as a batch reactor, comprises a reaction chamber provided with a bottom made up of a porous glass disk. The chamber is charged with the catalyst supported on a suitable carrier and superimposed thereon the substrate. The top of the chamber is provided with a thermometer fitted in an opening which can also serve as a sample port by removing the thermometer. The lower portion of the chamber is provided with a conduit having a flow control device to regulate the rate of flow of deuterium gas through the porous glass disk, and the upper portion of the chamber is fitted with a second conduit which is connected with a reflux condenser. The lower portion of the chamber and conduit, if desired, are placed in an oil bath which can be regulated to the selected reaction temperature. Alternatively the oil bath could be replaced by other suitable heating elements such as an electrical element.

The above reactor can be modified for use as a co-current reactor by adding the deuterium gas and the liquid to be exchanged at a fixed rate through the top port to the top of a heated catalyst bed. The effluent flowing from the bottom of the reactor is collected and either manually or automatically, such as by means of a circulatory pump, recycled back into the reactor until material of the desired isotopic purity is obtained.

The above reactor can also be modified for use as a countercurrent reactor wherein the substrate is added in a continuous stream through the top port and the deuterium gas simultaneously added through a port in the bottom of the apparatus.

The apparati described may be used for the preparation of up to several hundred grams of deuterated material and is subject to easy scale-up if larger quantities are desired.

In each system a supplementary source of deuterium, such as a partially or fully deuterated non-functional group-containing hydrocarbon, can be employed, but its use is not essential to the successful deuteration of the functional group-containing hydrocarbons by the method of this invention.

The exchange technique described is applicable to a wide range of organic structural types and yields deuterated compounds of any desired degree of isotopic purity up to and including substances in which substantially all hydrogen atoms are replaced by deuterium. The process utilizes deuterium gas, a relatively inexpensive source of label and is preferable to the tedious and expensive synthetic procedures which in many cases would otherwise be required.

A significant feature of the present process is that by the proper choice of catalyst and exchange temperature (which may be from about ambient to 300° C. but preferably in the range of 200° C. to 250° C.) decomposition of the starting substance is minimized and highly deuterated material is obtained. The present process can, therefore, be used to prepare compounds of any desired isotopic purity between 50 to 99.5 atom % D.

It will be appreciated by those knowledgeable in this discipline that material less than 100% isotopic purity contains a mixture of isotopic species. Any highly deuterated compound contains, by definition, little hydrogen, and therefore consists of a large proportion of the specie containing no hydrogen and smaller amounts of less well deuterated species. In contrast, a compound of low isotopic purity contains large proportions of material containing only hydrogen and varying amounts of species with one, two, three, etc. deuterium atoms per molecule. Thus bis(2-ethoxyethyl)ether (99 atom % D) consists of several isotopic species including bis(2-ethoxyethyl)ether-$d_{18}$ whose relative proportions are such that there remains only 1% of the hydrogen originally present. Similarly, diethylsebacate (95 atom % D) contains 95% deuterium atoms for every 5% hydrogen atoms present.

Highly deuterated compounds are valuable chemicals used in many kinds of highly specialized research work. General applications include their use in the study of reaction mechanisms, as tracers in the study of separation processes, and as model compounds for investigation of the physical properties of labelled compounds. These compounds can also be used as high temperature solvents for organic reactions, as convenient sources of deuterated low molecular weight compounds and certain compounds can be used as lubricating oils or as base fluids for lubricating greases. Examples of their use as a source of deuterated low molecular weight compounds include formation of deuterated ethyl groups by the reaction of bis(2-ethoxyethyl)ether (99 atom % D) with HCl, and hydrolysis of deuterated dibutylsebacate which yields deuterated butanol and sebacic acid. These deuterated products may then be employed as reagents for further syntheses.

As stated previously the novel process of the present invention permits the preparation of a wide variety of saturated, substantially fully labelled functional group-containing hydrocarbons having a boiling point of at least 100° C. Although the elapsed time required to prepare certain labelled compounds can be several weeks, the process requires very little attention once in operation, except for the periodic withdrawal of samples of analysis.

A further advantage of the process of the present invention resides in the fact that unsaturated functional group-containing hydrocarbons will ultimately lead to their fully saturated, labelled counterparts if required. Presumably, the unsaturated starting hydrocarbon is first reduced with deuterium to the saturated, partially labelled compound which then goes on to be substantially completely exchanged, if desired.

A still further advantage of the process of the present invention is that no cracking or isomerization of the substrate is observed under the conditions of exchange. The recovered labelled products are homogenous by vapor phase chromatography and possess sharp melting points and correct boiling points. Further, it was found that mass spectra corroborate the structures and isotopic content of the fully labelled compounds.

The process for preparing the labelled products of the present invention will be more fully understood by referring to the following examples.

EXAMPLE 1

Palmitic acid-$d_{32}$

With the deuterium inlet fully closed, 10 g. of 6% Pd on activated carbon were introduced into a batch reactor of 30 ml. volume via the thermometer port. Palmitic acid (20 g.) was added, the thermometer assembly inserted into the cell, and a water cooled condenser attached to the condenser arm and fitted with an exit tube for deuterium gas exhaust. The cell assembly was lowered into a thermostated oil bath and kept at 195° C. and deuterium gas then bubbled through the cell via the control at a rate of 40 ml./min.

Periodically samples were taken for analysis by raising the batch reactor out of the bath, shutting off the deuterium flow, and extracting (with syringe) a sample via the thermometer port. The system was then started up again as described above.

After 23 days of exchange it was determined by mass spectral analysis that the palmitic acid contained 96 atom % D, yield, 7 g. (38%), m.p. 63° C.

By repeating the process of Example 1 except for the catalyst that is replaced by an equivalent quantity of 5% ruthenium on carbon, palmitic acid-$d_{32}$ of 99 atom % D is obtained after 25 days of exchange at 195° C.

Other compounds prepared in substantially the same manner described in Example 1 are shown in Table I.

TABLE I

| Ex. No. | Starting Material | End Product (Atom % D) | b.p. °C. | Yield % | Exchange Time Days | Temp. °C. | $D_2$ Flow Rate ml/min |
|---|---|---|---|---|---|---|---|
| 2 | Lauric acid | Lauric acid (68) | 44 (m.p.) | 40 | 38 | 195 | 40 |
| 3 | Dibutyl-sebacate | Dibutylsebacate (86) | 338–342 | 50 | 38 | 150 | 40 |
| 4 | Di-n-octyl-ether | Di-n-octyl-ether (87) | 285–287 | 35 | 5 | 195 | 40 |
| 5 | Ethyl laurate | Ethyl laurate (91) | 240–242 | 37 | 18 | 195 | 40 |

EXAMPLE 6

Di-n-octylether-$d_{34}$.

Di-n-octylether was added at a rate of 120 to 180 drops per minute to a co-current reactor containing 6% Pd/C (10 g.) maintained at 150° C. and through which deuterium gas was continuously passed at a rate of 150 ml./minute. The reactor was equipped with a pump to automatically recycle liquid substrate through the catalyst tower. A total of 27.8 g. of di-n-octylether was added to the system at the start of the process and after 6 days of exchange 16.05 g. of di-n-octylether of 98.5 atom % D was obtained. The structure and isotopic purity was confirmed by mass spectral analysis.

Other compounds deuterated by substantially the same procedure as described in Example 6 are identified in Table II.

EXAMPLE 17

Bis(2-ethoxyethyl)ether-$d_{28}$

Substantially the same procedure described in Example 6 was followed for exchange of bis(2-ethoxyethyl)ether except that 15 g. of 6% Pd/C and 36.1 g. of the ether were used. After 7 days of exchange at 200° C., 22.1 g. of bis(2-ethoxyethyl)ether of 99.2 atom % D, b.p. 189°–190° C., was obtained.

A separate exchange was carried out with bis(2-ethoxyethyl)ether following the same procedure except that at 3% rhodium on carbon catalyst was employed. After 10 days of exchange at 200° C. there is obtained bis(2-ethoxyethyl)-ether of 99 atom % D.

EXAMPLE 18

1-Dodecanol-$d_{26}$

A solution of 1-dodecanol (20 g.) and n-dodecane (61 atom % D, 20 g.) was added to a batch reactor

TABLE II

| Ex. No. | Starting Material | End Product (Atom % D) | b.p. °C. | Yield % | Exchange Time | Temp. °C. | $D_2$ Flow Rate ml/min |
|---|---|---|---|---|---|---|---|
| 7 | Diethylsebacate | Diethylsebacate-$d_{26}$ (95) | 298–302 | 15 | 3 days | 250 | 150 |
| 8 | Diethylsebacate | Diethylsebacate (46) | 3 | 50 | 6 hrs. | 200 | 70 |
| 9 | Diethylsebacate[1] | Diethylsebacate (25) | 3 | 50 | 6 hrs. | 200 | 70 |
| 10 | Dipropyladipate[1] | Dipropyladipate (75) | 152–153 at 16 mm. | 40 | 24 hrs. | 200 | 70 |
| 11 | Tripropionin[2] | Tripropionin-$d_{26}$ (96) | 176–181 at 20 mm. | 25 | 17 days | 200 | 150 |
| 12 | Di-n-octyl-ether | Di-n-octyl-ether-$d_{34}$ (98.5) | 3 | 50 | 5 days | 200 | 150 |
| 13 | Bis(2-ethoxyethyl)-ether | Bis(2-ethoxyethyl)ether-$d_{18}$ (99.2) | 3 | 55 | 6 days | 200 | 150 |
| 14 | Bis(2-methoxyethyl)-ether | Bis(2-methoxyethyl)ether-$d_{14}$ (99.5) | 3 | 30 | 6 days | 200 | 150 |
| 15 | Triglyme (triethylene glycol dimethyl ether) | Triglyme-$d_{18}$ (99.5) | 274–276 | 7 | 8.5 days | 200 | 150 |
| 16 | N,N-dimethylacetamide[4] | N,N-dimethylacetamide-$d_9$ (99) | 165 | 40[5] | 21 days[6] | 200 | 150 |

[1] 28% Ni/Kieselguhr catalyst used.
[2] Tripropionic acid ester of glycerol.
[3] Structure and isotopic content confirmed by mass spectral analysis.
[4] 28% Ni/Kieselguhr (40 g.) catalyst used. This starting substance was also exchanged in presence of 6% Pd/C catalyst with substantially the same results.
[5] Yield: Major loss of deuterated material due to entrainment in $D_2$ gas leaving the exchange apparatus. Most of this can be recovered by placing a −70°C. trap after the condenser. Recovered material can be returned to exchange system or reserved for a new batch.
[6] Time: Exchange time can be shortened by replacing or reactivating the catalyst at any arbitrary level of deuteration.

containing 3% Pd/C (25 g.). The reactor was heated to 195° C. and deuterium gas passage at 60 ml./minute maintained for 31 days after which the products were separated on silica gel to yield 3.3 g. 1-dodecanol-$d_{26}$ of 99 atom % D, m.p. 25° C., and n-dodecane (99 atom % D).

EXAMPLE 19

Di-n-octylether-$d_{34}$

By following substantially the same procedure described in Example 6 but replacing the starting material and the catalyst employed therein by an equivalent quantity of di-n-octylether and 5% rhenium on carbom (3.7 g.) there is obtained di-n-octylether-$d_{34}$ of 99 atom % D after 10 days of exchange at 200° C. The structure and isotopic purity was confirmed by mass spectral analysis.

EXAMPLE 20

Stearic acid-$d_{36}$

Using the procedure described in Example 1 and substituting therein 20 g. of a purified commercial grade of oleic acid (cis-9-octadecenoic) acid for the palmitic acid and employing 5 g. of catalyst and adjusting the deuterium flow rate to 150 ml./minute, there is obtained after 15 days of exchange a 55% yield of stearic acid of 99 atom % D.

EXAMPLE 21

Ethyl stearate-$d_{40}$

Using the procedure described in Example 1 and substituting therein 20 g. of ethyl oleate for the palmitic acid and employing 5 g. of catalyst and adjusting the deuterium flow rate to 150 ml./minute, there is obtained after 17 days of exchange a 50% yield of ethyl stearate of 99 atom % D.

We claim:

1. A process for preparing a deuterated, saturated, acyclic hydrocarbon $C_{4-18}$-alkanoic acid or its ester or amide and having a boiling point of at least 100°C. in its liquid state, which comprises the continuous passage under atmospheric pressure of deuterium gas at a flow rate of at least about 40 ml. per minute through a saturated acyclic hydrocarbon alkanoic acid or its ester or its amide in its liquid state and a catalyst selected from the group consisting of palladium, platinum, rhodium, ruthenium, osmium, iridium, nickel, and rhenium at a temperature between about 100°C. and 300°C. and below the boiling point of said acyclic hydrocarbon acid, ester or amide and continuing the exchange until between 50 and 99.5% of the substrate hydrogen atoms have been replaced by deuterium atoms.

2. A process as claimed in claim 1 wherein a partially or fully deuterated non-functional group-containing hydrocarbon is employed as a supplementary source of deuterium.

3. A process as claimed in claim 1 wherein the functional group-containing hydrocarbon is a $C_{4-18}$ alkanoic acid.

4. A process as in claim 1 wherein the hydrocarbon substrate is palmitic acid thus providing palmitic acid-$d_{32}$.

5. A process as in claim 1 wherein the hydrocarbon substrate is lauric acid thus providing lauric acid with at least 68 atom % D.

6. A process as in claim 1 wherein the hydrocarbon substrate is stearic acid thus providing stearic acid-$d_{36}$.

7. A process as in claim 1 wherein the hydrocarbon substrate is a lower alkyl ester of a $C_{4-18}$-alkanoic acid.

8. A process as in claim 1 wherein the hydrocarbon substrate is ethyl laurate thus providing ethyl laurate with at least 91 atoms % D.

9. A process as in claim 1 wherein the hydrocarbon substrate is ethyl stearate thus providing ethyl stearate-$d_{40}$.

10. A process as in claim 1 wherein the hydrocarbon substrate is N,N-dimethylacetamide thus providing N,N-dimethylacetamide-$d_9$.

* * * * *